United States Patent [19]

Sun

[11] Patent Number: 4,626,610

[45] Date of Patent: Dec. 2, 1986

[54] IRON DEFICIENCY CHLOROSIS RESISTANT SOYBEAN VARIETY

[75] Inventor: Paul Sun, Roscoe, Ill.

[73] Assignee: DeKalb-Pfizer Genetics, DeKalb, Ill.

[21] Appl. No.: 690,706

[22] Filed: Jan. 11, 1985

[51] Int. Cl.⁴ ............................................... A01H 1/06
[52] U.S. Cl. ........................................... 800/1; 47/58
[58] Field of Search ............................... 47/58; 800/1

[56] References Cited

U.S. PATENT DOCUMENTS 4,545,146 10/1985 Davis ..................................... 47/58

Primary Examiner—Robert E. Bagwill
Attorney, Agent, or Firm—Charles J. Knuth; Peter C. Richardson; James H. Monroe

[57] ABSTRACT

A soybean variety which is a high yielder and resistant to iron deficiency chlorosis.

7 Claims, No Drawings

IRON DEFICIENCY CHLOROSIS RESISTANT SOYBEAN VARIETY

BACKGROUND OF THE INVENTION

Iron deficiency chlorosis in soybeans occurs in the northern U.S. in soils having a high pH. These soils are known as calcareous, high-lime or alkaline soils and they are especially prevalent in northern Iowa and southern and western Minnesota, important soybean growing areas. The condition is observed first as a yellowing of the trifoliate leaves and it results in a lowered yield.

Up to the present time the farmer has had two choices in dealing with this problem. He could choose seeds of a variety known to be resistant in some degree to the condition or he could spray the young plants with a foliar iron spray. The known resistant varieties often suffer from some other disadvantage and the application of foliar iron is both expensive and exacting. In fact, is it well known in the art that the best time to apply foliar iron spray is just before the leaves begin to yellow. Any degree of yellowing leads to reduced yield.

SUMMARY OF THE INVENTION

The present invention comprises a novel variety of soybean, CX174, which is both resistant to iron deficiency chlorosis and is a high yielder. This invention also comprises a novel process to produce the seeds of a soybean variety resistant to iron deficiency chlorosis comprising the steps of:

(a) crossing plants grown from seeds of Beeson and Corsoy;

(b) developing a pure line from the seeds produced in (a) and crossing plants grown from this line with plants grown from the seeds of Hodgson;

(c) developing a pure plant variety from the seeds produced in (b) selected from those resistant to iron deficiency chlorosis; and (d) harvesting the seeds of the pure resistant variety thus produced.

The process is preferred wherein the selection is done by growing plants on calcareous soil and selecting those that are green at an early trifoliate stage of growth. The selection is preferably carried out after the variety has been developed but the selection can be performed first and the variety developed subsequently. The seeds produced by this process are also a part of this invention. Finally, the novel soybean variety CX174 which is resistant to iron deficiency chlorosis is claimed as a part of this invention.

DETAILED DESCRIPTION OF THE INVENTION

Soybean varieties which have specific, desirable traits are often developed by normal plant breeding techniques. Two varieties will usually be selected for certain characteristics and they will be crossed, one variety being employed as male and the other as female. After the first cross, the $F_1$ generation plants will usually be screened for a general, overall healthy appearance and thrifty growth habit. Seeds will be saved from the $F_1$ plants selected and subsequent generations will be grown up, again selecting desirable plants from each generation. At about the $F_5$ generation level, the particular trait sought will usually be tested for by applying stress. For example, if disease resistance is the desired trait, the plants will be infected and seeds of those plants which are resistant will be saved. If herbicide resistance is the characteristic wanted, the plants will be sprayed with herbicide and seeds of the survivors will be saved. In the case of iron deficiency chlorosis, plants will be grown in calcareous soils and those plants which are still a healthy green color at an early trifoliate stage will be grown to maturity and their seeds will be saved.

In the particular case of the process of this invention for producing a soybean variety resistant to iron deficiency chlorosis, two commercially available varieties, Beeson and Corsoy, were crossed to produce an experimental line which was used later as the male parent. This experimental line was not an outstanding performer and it was not preserved. Another commercially available variety, Hodgson, was employed as the female in the cross which led to the resistant variety. It is interesting and most surprising to note that none of the three commercially available varieties used in the invention is resistant to iron deficiency chlorosis.

From this cross between Hodgson and the experimental male, a line was developed by the normal plant breeding means of growing out the seeds, examining the resulting plants and selecting these with outstanding growth characteristics and again saving those seeds. At the $F_5$ generation level, seeds of this now true-breeding line were planted on high pH, calcareous soil. The plants were seen to be green at the trifoliate stage of growth which indicates that they are resistant to iron deficiency chlorosis.

While in this work the selection for resistance was done after the line was stabilized, the procedure could have been reversed; i.e., the calcareous soil stress could have been applied to the $F_2$ generation and only resistant plants could have been developed into true-breeding varieties. In like manner, although Hodgson was employed as the female, the Beeson-Corsoy derived experimental line could have been employed as the female and Hodgson could have served as the male. The present invention encompasses these alternative possibilities.

Soybean variety CX174 is an indeterminant Group I maturing variety which matures about two days earlier than Corsoy 79. It has purple flowers, gray pubescence and tan pods at maturity. The seeds have a dull seedcoat luster with buff hila. The leaves are of medium size and are ovate in shape. Seeds of CX174 have been deposited with the National Seed Storage Laboratory, Colorado State University, Ft. Collins, Colo. under NSSL Ser. No. 191810.

The variety has excellent resistance to iron deficiency chlorosis and thus performs well on calcareous soils; it is susceptible to phytophthora root rot. Table 1 below compares performance data of CX174 and Weber, another early maturing variety. The comparison was done in northern Iowa.

TABLE 1

| Variety | No. of Tests | Height | Date Mature | Lodging Index | Seed Size g./100 Seeds | Yield bu./acre |
|---|---|---|---|---|---|---|
| CX174 | 3 | 34 | 9/29 | 1.6 | 19.8 | 46.4 |
| Weber | 3 | 37 | 9/26 | 3.1 | 13.4 | 43.6 |

Variety CX174 was developed by crossing two public varieties, Beeson and Corsoy, to produce an experimental line to serve as the male parent. This line was not outstanding in performance and has not been preserved.

Hodgson, another public variety, was employed as the female parent. Three $F_1$ seeds were produced from this initial cross and they were grown and the plants compared and harvested in bulk. $F_2$, $F_3$ and $F_4$ generations were grown with plants being selected from each generation for generally desirable characteristics.

At the $F_5$ generation, seeds of CX174 were sent to locations known to have calcareous soil and were grown there. The variety was observed to have excellent resistance to iron deficiency chlorosis. Subsequently the variety was increased and the chlorosis resistance was confirmed by additional testing.

I claim:

1. A novel process to produce the seeds of a soybean variety resistant to iron deficiency chlorosis comprising the steps of:
    (a) crossing plants grown from seeds of Beeson and Corsoy;
    (b) developing a pure plant line from the seeds produced in (a) and crossing plants grown from said line with plants grown from seeds of Hodgson;
    (c) developing a pure plant variety from the seeds produced in (b), said variety being selected for those resistant to iron deficiency chlorosis; and
    (d) harvesting the seeds of said pure resistant plant variety.

2. The process of claim 1 wherein a pure plant variety is first developed from the seeds produced in (b) and said pure plant variety is subsequently subjected to selection for those resistant to iron deficiency chlorosis.

3. The process of claim 1 wherein a plant line selected for resistance to iron deficiency chlorosis is first developed from the seeds produced in (b) and said resistant plant line is subsequently developed into a pure plant variety.

4. The process of claim 1 wherein Hodgson is employed as the female in step (b).

5. The process of claim 1 wherein said selection in (c) is performed by growing plants on calcareous soil and selecting those that are green at an early trifoliate growth stage.

6. Seeds produced according to the process of claim 1.

7. Novel soybean variety CX174.

* * * * *